(12) United States Patent
Sakamoto et al.

(10) Patent No.: US 8,426,640 B2
(45) Date of Patent: Apr. 23, 2013

(54) METHOD FOR PRODUCING ACRYLIC ACID, AND METHOD FOR PRODUCING HYDROPHILIC RESIN AND METHOD FOR PRODUCING WATER-ABSORBING RESIN USING PRODUCTION METHOD THEREOF

(75) Inventors: Kazuhiko Sakamoto, Himeji (JP); Masaru Ishikawa, Himeji (JP)

(73) Assignee: Nippon Shokubai Co., Ltd., Osakak (JP)

( * ) Notice: Subject to any disclaimer, the term of this patent is extended or adjusted under 35 U.S.C. 154(b) by 0 days.

(21) Appl. No.: 12/989,553

(22) PCT Filed: Apr. 24, 2009

(86) PCT No.: PCT/JP2009/058147
§ 371 (c)(1),
(2), (4) Date: Jan. 10, 2011

(87) PCT Pub. No.: WO2009/133813
PCT Pub. Date: Nov. 5, 2009

(65) Prior Publication Data
US 2011/0118426 A1    May 19, 2011

(30) Foreign Application Priority Data
Apr. 27, 2008 (JP) ................. 2008-116504

(51) Int. Cl.
C07C 51/42    (2006.01)
C08F 20/06    (2006.01)

(52) U.S. Cl.
USPC ........................ 562/600; 526/317.1

(58) Field of Classification Search .......... None
See application file for complete search history.

(56) References Cited

U.S. PATENT DOCUMENTS

| | | | |
|---|---|---|---|
| 5,208,370 A | 5/1993 | Bauer, Jr. et al. | |
| 2004/0249199 A1 | 12/2004 | Ueno et al. | |
| 2007/0129572 A1 * | 6/2007 | Shibusawa et al. | ........... 562/600 |

FOREIGN PATENT DOCUMENTS

| | | |
|---|---|---|
| EP | 0 551 111 | 1/1993 |
| JP | 47-017714 | 9/1972 |
| JP | 49-134622 | 12/1974 |
| JP | 61-218556 | 9/1986 |
| JP | 5-339199 | 12/1993 |
| JP | 09-093027 | 4/1997 |
| JP | 2003-160532 | 6/2003 |
| JP | 2003-246810 | 9/2003 |
| JP | 2005-15478 | 1/2005 |
| WO | 01/98382 | 12/2001 |
| WO | 2006/019842 | 2/2006 |
| WO | 2006/109842 | 10/2006 |

* cited by examiner

*Primary Examiner* — Karl J Puttlitz
(74) *Attorney, Agent, or Firm* — Occhiuti Rohlicek & Tsao LLP (57) ABSTRACT

[Problem]
There is provided, in a process for producing acrylic acid having a catalytic gas-phase oxidation reaction step, a condensation step, a collection step, a distillation step, a crystallization step, an acrylic acid recovering step or the like, a production method for acrylic acid, in which contamination of acrylic acid with protoanemonin without providing any additional purification treatment to the resultant purified acrylic acid can be reduced.

[Solution]
The problems described above can be solved by providing the production method for acrylic acid comprising A) a step obtaining an acrylic acid-containing gas by a catalytic gas-phase oxidation reaction of gas containing a acrylic acid raw material; B) a step of obtaining the acrylic acid-containing solution by introducing the acrylic acid-containing gas to the collection column or the condensation column and performing collection or condensation; C) a step of obtaining the crude acrylic acid by introducing the acrylic acid-containing solution to the distillation column or the crystallizer and performing distillation or crystallization, wherein a step of heat treating the acrylic acid-containing solution or the crude acrylic acid containing 100 ppm by mass or more of protoanemonin, under the condition of 100° C. or more of temperature, 1 hour or more of time and a step of introducing the heat-treated acrylic acid-containing solution or the crude acrylic acid to the collection column, the condensation column, the distillation column or the crystallizer, are included.

4 Claims, 2 Drawing Sheets

METHOD FOR PRODUCING ACRYLIC ACID, AND METHOD FOR PRODUCING HYDROPHILIC RESIN AND METHOD FOR PRODUCING WATER-ABSORBING RESIN USING PRODUCTION METHOD THEREOF

CROSS REFERENCE TO RELATED APPLICATIONS

This application is a National Stage of International Application No. PCT/JP2009/058147, filed on Apr. 24, 2009, which claims priority to Japanese Application No. 2008-116504 filed Apr. 27, 2008. The content of the prior applications are incorporated herein by reference in their entirety.

TECHNICAL FIELD

The present invention relates to a method for producing acrylic acid, and a method for producing a hydrophilic resin and a method for producing a water-absorbing resin using the production method thereof.

BACKGROUND ART

By performing a catalytic gas-phase oxidation of at least one or more acrylic acid raw material selected from the group consisting of propane, propylene and acrolein (hereinafter, referred to as "propylene etc.") by a molecular oxygen-containing gas in the presence of oxidation catalyst, in addition to acrylic acid as the object, by-products such as acetic acid, formaldehyde, acrolein, propionic acid, maleic acid, acetone, furfural, benzaldehyde, protoanemonin, and mixed gas containing impurities are obtained as a reaction product. Next, the purified acrylic acid can be obtained by purifying this reaction product by various purification methods to remove these by-products and impurities.

For example, in a method for producing acrylic acid industrially by the catalytic gas-phase oxidation of propylene etc. by molecular oxygen-containing gas, there is a method that an aqueous solution containing acrylic acid and by-product such as acetic acid is obtained by a step that mixed gas obtained by performing the catalytic gas-phase oxidation is introduced into a collection column, where contacting with an aqueous solution for collection such as water, cooling, and absorbing for collection are carried out, then, acrylic acid is separated from this aqueous solution by distillation or the like, and is purified to obtain the purified acrylic acid.

Further specifically, as a method to obtain the high-purity acrylic acid as a product from the above aqueous solution containing acrylic acid, there are a method that, in azeotropic separation column, the high-purity acrylic acid substantially not containing acetic acid, water and poor water-soluble solvent can be recovered from the column bottom by distilling using poor water-soluble solvent (for example, refer to: JP-A-5-246941, EP-0551111-A1); a method that the purified acrylic acid having high-purity can be obtained by a comparatively easy step by introducing an acrylic acid-containing solution obtained from the collection step to a crystallization step (for example, refer to: JP-A-2005-15478, US-2004249199 A1), or the like.

However, in the purified acrylic acid obtained from the above method, there still exist minor amount of impurities which is difficult to be completely removed by conventional distillation and/or crystallization. These impurities are known to have a drawback that induction time in polymerization reaction is forced to lengthen when acrylic acid is homopolymerized or copolymerized with the monomer co-polymerizable with this monomer, or they perform an action of chain-transfer agent resulting in the formation of polymer having low polymerization degree (for example, refer to JP-A-61-218556). Various measures that for aiming to prevent the polymerization delay caused by among the various impurities, particularly, protoanemonin, this protoanemonin in the purified acrylic acid is removed, or the concentration of protoanemonin is reduced, are provided. It should be noted that, protoanemonin is known to have an effect of polymerization inhibition for the acrylic acid-containing solution (for example, refer to: JP-A-47-17714).

As a method for treating the above protoanemonin, specifically, following methods are provided.

(1) a method that the impurities (protoanemonin) contained in the crude acrylic acid obtained by catalytic gas-phase oxidation of propylene or acrolein are treated with aqueous solution of bisulfite in the purification step thereof, and further, are treated with hydrazine compounds (for example, refer to: JP-A-61-218556);

(2) a method that impurities (protoanemonin) contained in the crude methacrylic acid obtained by catalytic gas-phase oxidation of isobutylene or the like is treated with the aqueous solution of bisulfite in the purification step thereof (for example, refer to: JP-A-59-93027);

(3) a method that an effective amount of p-phenylene diamine and the salt thereof are added to aqueous solution of methacrylic acid (for example, refer to JP-3359368);

(4) a method that super purified acrylic acid is obtained further by reducing protoanemonin from the purified acrylic acid with performing additional purification treatment such as increase of theoretical plate number, increase of reflux ratio in distillation column, and increase of crystallization times, or super purified acrylic acid is obtained further by strong alkaline treatment of this product (for example, refer to: WO 01/098382).

DISCLOSURE OF INVENTION

However, there is a problem that in the production method of acrylic acid by using the method of reducing the above conventional various impurities (particularly, protoanemonin), expensive chemicals are needed in each method, also, chemical treatment is needed after use thereof, and equipment cost and utilities cost become too high in the super purification by distillation or crystallization. Further, when the improvement only of removal ratio of these various impurities is focused on, there is a problem that yields resultant acrylic acid decrease.

Therefore, it is an object of the present invention to provide a production method for acrylic acid in which impurities (particularly protoanemonin) can be reduced at low-cost and in easy method, and further, yield was enhanced, without using particular chemicals.

In more detail, it is to provide the production method for acrylic acid in which the impurities (particularly protoanemonin) can be reduced, by adding simple improvement only to the conventional production process of acrylic acid including the step for generating acrylic acid by catalytic gas-phase oxidation of propylene etc.; next, the step of collecting said acrylic acid by absorption, collection and/or condensation; next the step of purification to obtain purified acrylic acid from the collected acrylic acid.

Object of the present invention is accomplished by providing Production method for acrylic acid comprising:

A) a step of obtaining an acrylic acid-containing gas by catalytic gas-phase oxidation reaction of a gas containing an acrylic acid raw material;

B) a step of obtaining an acrylic acid-containing solution by introducing the acrylic acid-containing gas to a collection column or a condensation column and performing collection or condensation;

C) a step of obtaining a crude acrylic acid by introducing the acrylic acid-containing solution to the distillation column or the crystallizer and performing distillation or crystallization, wherein a step of heat treating the acrylic acid-containing solution or the crude acrylic acid, containing 100 ppm by mass or more of protoanemonin, under the condition of 100° C. or more of temperature, 1 hour or more of time and a step of introducing the acrylic acid-containing solution or the crude acrylic acid, having been heat treated, to the collection column, the condensation column, the distillation column or the crystallizer, are included in the production method.

By using the method of the present invention, amount of impurities (particularly protoanemonin) produced in the process of acrylic acid can be reduced, therefore, the contamination of acrylic acid by the impurities (particularly protoanemonin) can be alleviated. In more detail, according to the present invention, the production method for acrylic acid that the impurities (particularly protoanemonin) can be reduced at low cost and in easy method without using of particular chemicals and yield is improved, can be provided.

It should be noted that, the impurities (particularly protoanemonin) may be simply referred to as "protoanemonin".

BEST MODE FOR CARRYING OUT THE INVENTION

The First Aspect of the Present Invention

The first aspect of the present invention is Production method for acrylic acid comprising: A) a step of obtaining an acrylic acid-containing gas by catalytic gas-phase oxidation reaction of a gas containing an acrylic acid raw material; B) a step of obtaining an acrylic acid-containing solution by introducing the acrylic acid-containing gas to a collection column or a condensation column and performing collection or condensation; C) a step of obtaining a crude acrylic acid by introducing the acrylic acid-containing solution to the distillation column or the crystallizer and performing distillation or crystallization, wherein a step of heat treating the acrylic acid-containing solution or the crude acrylic acid, containing 100 ppm by mass or more of protoanemonin, under the condition of 100° C. or more of temperature, 1 hour or more of time and a step of introducing the acrylic acid-containing solution or the crude acrylic acid, having been heat treated, to the collection column, the condensation column, the distillation column or the crystallizer, are included in the production method.

The present invention is characterized in that the acrylic acid-containing solution obtained by collecting or condensing the acrylic acid-containing gas, or the crude acrylic acid obtained by distillation or crystallizing the acrylic acid-containing solution, or the residue of distillation or the mother liquid of crystallization to be described later are treated under the condition of heating at predetermined temperature in predetermined hour (hereinafter, "heat-treatment at predetermined temperature in predetermined hour" may be simply referred to as "heat-treatment of the present invention"), then, are introduced in the collection column, the condensation column, the distillation column or the crystallizer. That is, the present invention is characterized in that in the system for producing acrylic acid, the acrylic acid-containing solution generated, the crude acrylic acid, the residue of distillation or the mother liquid of crystallization are subjected to the heat-treatment of the present invention, and then, are introduced (circulated) to the collection column, the condensation column, the distillation column or the crystallizer (hereinafter, "the collection column, the condensation column, the distillation column or the crystallization column" may be generally referred to as "the inside of the system"). It should be noted that, "the inside of the system" described in the present description means the concept which includes not only "the collection column, the condensation column, the distillation column or the crystallization column", but also all the inside of the system of the process in the production method for acrylic acid in the present invention. That is, in the process of the production method for acrylic acid of the present invention, even when the devices (for example, the acrolein diffusion column or the acrylic acid recovering column) other than "the collection column, the condensation column, the distillation column or the crystallization column" are present, they are included to the technical scope of the present invention.

When the purified acrylic acid is conventionally produced, for example, by additional treatment such as increase of number of the theoretical plates, increase of the reflux ratio in the distillation column, increase of the crystallization times, protoanemonin in acrylic acid is removed to obtain the super purified acrylic acid.

In the method for the present invention, the production step of acrylic acid can be simplified without the need for these additional purification treatments. In addition, since content of protoanemonin is significantly reduced in acrylic acid produced by the method according to the first aspect of the present invention, when it the acrylic acid is used as a raw material for polymer of acrylic acid, stable polymerization operation can be carried out without causing the delay problem of polymerization. According to the present invention, specific impurities (protoanemonin), which was difficult to remove by the conventional distillation and/or crystallization, can be reduced by the simple method at low cost without using the particular chemicals.

Hereinafter, the present invention is described in detail referring to the drawing accordingly. It should be noted that, following embodiment is only one specific examples of the present invention, it is understood that the present invention is not limited to such examples. In addition, each of the drawings is represented exaggeratedly for convenience, dimension ratio of each component unit in each drawing may be different to that of the actual.

It should be noted that, in the present description, "low boiling point substance" means a substance having lower boiling point than that of acrylic acid in the standard state, "high boiling point substance" means a substance having higher boiling point than that of acrylic acid in the standard state. "Condensable substance" means the substance which is a liquid at 20° C. in atmospheric pressure. "Distillation" means a method for separating the volatile components contained by heating the solution until the boiling point. "Diffusion" means a method for transferring the target product in the solution to gas-phase by supplying diffusion gas or heating.

"Crystallization" is an operation of precipitating crystal from liquid phase or gas-phase. In addition, "dynamic crystallization step" means a method for crystallization in which liquid phase is transferred with forced convection caused by pump or the like in crystallization. "static crystallization step" means a method for crystallization in which liquid phase is transferred with natural convection only without using pump or the like. In addition, when the theoretical number of plates in the distillation column or the collection column is set to n plates, "column top" means the part of one plate of the theoretical number of plates, "column bottom" means the part of "n plates" of the theoretical number of plates, and "other than column top" means the parts of 2 to n plates of the theoretical number of plates. In addition, in the present description, among the exhaust gas (exhaust gas from the column top of the collection column) from the column top of the collection column, exhaust gas introducing to the inside of the system containing the collection column is called as "recycled gas", and exhaust gas introducing to the outside of the system is called as "waste gas". In addition, in the present description, content of "protoanemonin" is represented by value measured by the method described in examples. In addition, in the present description, the low boiling point distillation column, the first high boiling point distillation column, and the second high boiling point distillation column may be simply referred to the distillation column simply. In addition, "low boiling point distillation column" may be referred to "azeotropic distillation column". More specifically, "the low boiling point distillation column" is the distillation column used for removing the low boiling point substance. "The low boiling point distillation column" is higher concept of "the azeotropic distillation column", particularly, when distilled by using one such as azeotropic solvent, this column is referred to "the azeotropic distillation column". In the present description, "distillation" is the concept contained in that distillation is carried out in any of "the low boiling point distillation column", "the first high boiling point distillation column" or "the second high boiling point distillation column".

Hereinafter, the production method for acrylic acid of the present invention is described in detail.

First Embodiment

The first embodiment of the present invention is the production method of acrylic acid including A) a step of obtaining an acrylic acid-containing gas by catalytic gas-phase oxidation reaction of a gas containing an acrylic acid raw material;

B) a step of obtaining an acrylic acid-containing solution by introducing the acrylic acid-containing gas to a collection column and performing collection;

C) a step of obtaining a crude acrylic acid by introducing the acrylic acid-containing solution to the low boiling point distillation column and performing distillation, C') a step of introducing the crude acrylic acid to the first high boiling point distillation column and performing distillation, D) a step of recovering a residue of distillation discharged from the high boiling point distillation column;

wherein a step of heat treating the acrylic acid-containing solution, the crude acrylic acid or the residue of distillation, containing 100 ppm by mass or more of protoanemonin, under the condition of 100° C. or more of temperature, 1 hour or more of time and a step of introducing the acrylic acid-containing solution, the crude acrylic acid, or the residue of distillation, having been heat treated, to the collection column, the low boiling point distillation column or the first high boiling point distillation column, are included in the production method.

(Step A)

Step A in first embodiment of the first aspect of the present invention, is a step of obtaining an acrylic acid-containing gas by catalytic gas-phase oxidation reaction of a gas containing an acrylic acid raw material.

Figure 1:
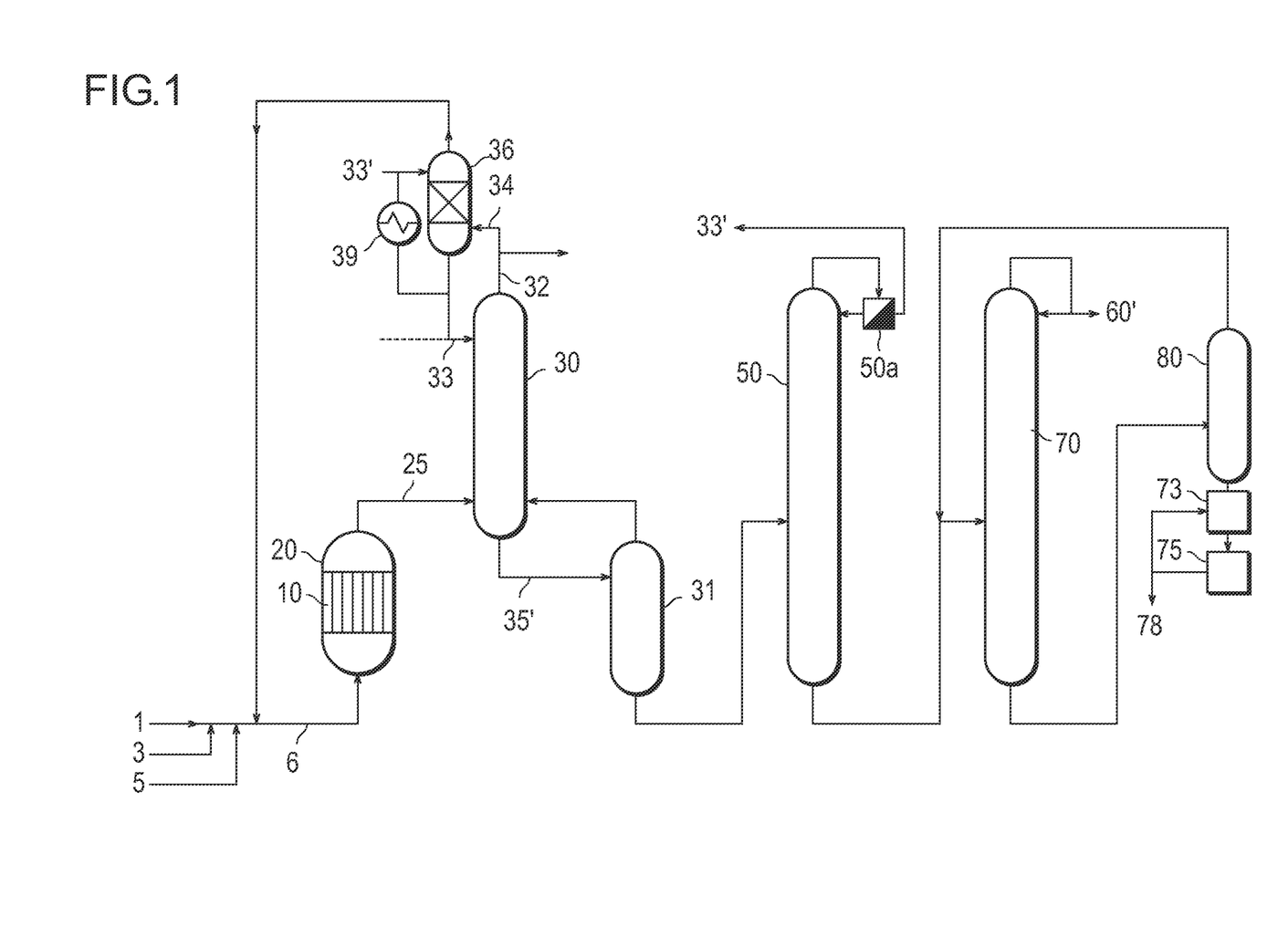
FIG. 1 is the schematic diagram showing the production equipment to be used in the first embodiment of the first production method for acrylic acid of the present invention.

As shown in FIG. 1, firstly, the acrylic acid raw material 1 and the molecular oxygen-containing gas 3, and dilution gas 5 are mixed to form mixed gas 6. It should be note that, the recycled gas 34 discharged from the column top of the collection column 30 in the step B to be described later can also be mixed with the acrylic acid raw material 1, the molecular oxygen-containing gas 3 and dilution gas 5 to form the mixed gas 6. By supplying this mixed gas 6 to the reactor 20 packed with the catalytic gas-phase oxidation catalyst 10, and by performing the catalytic gas-phase oxidation, the acrylic acid-containing gas 25 can be obtained.

The acrylic acid raw material 1 includes, for example, at least one kind selected from the group consisting of propane, propylene, and acrolein.

The molecular oxygen-containing gas 3 includes, for example, molecular oxygen or the like. As a supply source of said molecular oxygen, air can be used. It should be noted that, when said air contains water, it is preferable to be dehumidified previously before supplying to the reactor 20. Also, oxygen enriched air or pure oxygen can be used instead of air.

Dilution gas 5 is not particularly limited, and includes nitrogen, carbon dioxide, or the other inert gas or the like.

The reactor 20 is not particularly limited, as long as the catalytic gas-phase oxidation reaction can be carried out, but the multi-tubular reactor can be preferably used from the standpoint of excellent reaction efficiency.

The method for catalytic gas-phase oxidation is also not particularly limited, for example, can be carried out by method that the known catalyst of the catalytic gas-phase oxidation 10 is packed in the reactor 20, and the acrylic acid raw material gas 1, the molecular oxygen-containing gas 3, and dilution gas 5 can be contacted with the catalyst for oxidation. It should be noted that, when propylene is used as the acrylic acid raw material gas 1, 7 to 15% by volume of propylene concentration, 0 to 10% by volume of water content based on 100% by volume of mixed gas 6, and molecular oxygen in the range of 1:1.0 to 2.0=propylene:molecular oxygen (by volume ratio) are preferable. When propylene is used as the acrylic acid raw material gas 1, the catalytic gas-phase oxidation reaction is generally carried out by two steps, and two kinds of the catalytic gas-phase oxidation catalysts 10 is preferably used. The catalytic gas-phase oxidation catalyst 10 in the first step oxidizes the acrylic acid raw material gas 1 containing propylene in gas-phase to produce mainly acrolein. The catalytic gas-phase oxidation catalyst 10 in the second step oxidizes the acrylic acid raw material gas 1 containing acrolein in gas-phase to produce mainly acrylic acid. In addition, as the catalytic gas-phase oxidation catalyst 10 in the first step, the complex oxides containing iron, molybdenum, and bismuth can be preferably used, also, as the catalytic gas-phase oxidation catalyst 10 in the second step, one containing vanadium can be preferably used.

It should be noted that, in FIG. 1, the catalytic gas-phase oxidation reaction was shown by the embodiment to be carried out in the single reactor connected with one reactor 20, but may be carried out in the tandem type reactor connected with two different type reactor 20.

It should be noted that, step A of the present invention was described above, alternatively, the method described in JP-A-

2000-325795 (U.S. Pat. No. 6,383,973 B1) or the like can be used by reference accordingly.

(Step B)

Step B in the first embodiment of the first aspect of the present invention is a step of obtaining an acrylic acid-containing solution by introducing the acrylic acid-containing gas to a collection column and performing collection. The solution containing high concentration of acrylic acid can be obtained according to step B in the first embodiment of the first aspect of the present invention.

As shown in FIG. 1, the acrylic acid-containing gas 25 is supplied to the column bottom of the collection column 30, and aqueous solution 33 for collection is supplied from the column top of the collection column 30 to contact with the acrylic acid-containing gas 25, and to collect, then the acrylic acid-containing solution 35 can be obtained.

The collection column 30 is generally operated under higher than atmospheric pressure. Pressure of column top (gauge pressure) is preferably 0 to 0.4 MPa, more preferably 0 to 0.1 MPa, still more preferably 0 to 0.03 MPa. When pressure is less than 0 MPa (gauge pressure), pressure reducing device is needed, thus, equipment cost, utilities cost may be increased. On the other hand, when pressure is higher than 0.4 MPa (gauge pressure), it is needed to elevate temperature of the collection column 30 considerably, therefore, collection efficiency may be reduced. In addition, the column top temperature is generally 30 to 85° C., particularly preferably 40 to 80° C.

As contacting method for the acrylic acid containing gas 25 with aqueous solution for collection 33, the known contacting method can be used, for example, cross flow contact using bubble cap tray, uniflat tray, perforated plate tray, jet tray, bubble tray, Venturi tray; counter flow contact using turbo grid tray, dual flow tray, ripple tray, Kittel tray, regular packing or irregular packing such as gauze type, sheet type or grid type, are exemplified.

It should be noted that, among exhaust gas (exhaust gas from the column top of the collection column 32) from the column top of the collection column 30, recycled gas 34 only is introduced to the cooling tower 36 to cool down by gas-liquid contact with the water for collection 33' newly supplying to the inside of the system, and be concentrated to remove the condensable substances contained in the recycled gas 34. After that, it is preferable to circulate it to the reactor 20. It is because that, content of water contained in the recycled gas can be reduced, consequently, the acrylic acid-containing solution 35 containing high concentration of acrylic acid can be obtained from the column bottom of the collection column 30. Therefore, cooling method by using a combination of the cooling tower 36 and the cooling device 39 is preferable. It should be noted that, cooling of recycled gas only is preferable from the standpoint of improvement of the efficiency of acrylic acid collection. In addition, by cooling the recycled gas, not only water but also acid can be condensed, thus, acid content to be supplied to the reactor 20 can be reduced, and deterioration of the catalytic gas-phase oxidation catalyst being caused by acid can be preferably prevented.

As the water 33' for collection, the conventionally known one can be widely used as long as it is the aqueous solution which can collect acrylic acid. Specifically, water, the high boiling point solvent containing water can be exemplified. It should be noted that, as water, process water obtained in the production equipment of acrylic acid can be preferably used. Temperature of the water 33' for collection is 0 to 50° C., preferably 10 to 40° C. In the water 33' for collection, in order to inhibit the polymerization of polymerizable substance such as acrylic acid, one kind or more compounds selected from the group consisting of N-oxyl compound, phenol compound, manganese salt such as manganese acetate, copper dialkyldithiocalbamate such as copper dibutyldithiocalbamate, nitroso compound, amine compound and phenothiazine described in JP-A-2001-348360, JP-A-2001-348358, JP-A-2001-348359 or the like may be contained.

It should be noted that, when recycled gas is cooled to condense a condensable substance to form a condensate liquid and the condensate liquid is introduced to the reactor 20, water in the recycled gas can be preferably removed in advance so that water content of the acrylic acid raw material gas 1 to be supplied to the reactor 20 becomes 0 to 10% by volume, more preferably 0 to 7% by volume, particularly 0 to 6% by volume. It is because that, when the water content is over 10% by volume, loss ratio of acrylic acid may increase by the water to be supplied to the collection column 30 via reactor 20. In addition, total acid concentration is 0 to 0.2% by volume, more preferably 0 to 0.1% by volume. It is because that, when total acid concentration is over 0.2% by volume, deterioration of the catalytic gas-phase oxidation catalyst 10 may be accelerated. In the recycled gas, except for water and acid component, non-reacted propylene, acrolein, oxygen, dilution gas or the like are included. Amount of water contained in the recycled gas and amount of blending of the recycled gas to the raw material gas are calculated and concentration of propylene and concentration of oxygen contained in the recycled gas are calculated, so that the water concentration and the total acid concentration in the raw material gas become the above optimum range, and when concentration of propylene and concentration of oxygen to be supplied to the reactor 20 are determined, then, propylene concentration, oxygen concentration, water concentration, and total acid concentration can be easily adjusted. In addition, "total acid" is a compound having carboxyl group, and in the recycled gas, acrylic acid, formic acid, acetic acid, or the like are contained.

It should be noted that, the cooling method for the recycled gas is not particularly limited, the equipment in which condensable substance can be condensed, may be used. For example, multi-tublar type heat exchanger, fin-tube type heat exchanger, air-cooled type heat exchanger, double-pipe type heat exchanger, coil type heat exchanger, direct contact type heat exchanger, plate type heat exchanger or the like can be used.

In addition, the cooling temperature of the recycled gas is not particularly limited, the recycled gas is condensed by cooling so that the water concentration in total volume of the mixed gas 6 to be supplied to the reactor 20 become 0 to 10% by volume, more preferably 0 to 7% by volume, particularly 0 to 7% by volume, and still more preferably the total acid concentration become 0 to 0.2% by volume, more preferably 0 to 0.1% by volume. When air is used as the molecular oxygen-containing gas 3, water is contained in said gas. From blending volume of air and the above preferable water concentration and blending volume of mixed gas 6, water content in the recycled gas after cooling is calculated, thus, the recycled gas is cooled to obtain said water concentration. In the present invention, said recycled gas temperature is cooled 1 to 50° C. lower, more preferably 2 to 40° C. lower, particularly preferably 3 to 30° C. lower than the waste gas temperature.

In the first embodiment of first aspect of the present invention, the heat-treatment of the present invention is carried out to the acrylic acid-containing solution, the crude acrylic acid, or the residue of distillation. Here, in the acrylic acid-containing solution 35 obtained by collection, about 100 to about 500 ppm by mass of protoanemonin relative to the total mass of the acrylic acid-containing solution 35 may be contained.

Therefore, the heat-treatment of the present invention can be preferably carried out to the acrylic acid-containing solution obtained in step B of the first embodiment of the first aspect of the present invention. However, when the heat-treatment of the present invention is carried out to the crude acrylic acid to be described later, the heat-treatment of the present invention is not essential to the acrylic acid-containing solution. However, from the standpoint of producing the acrylic acid containing less amount of protoanemonin, the heat-treatment of the present invention is preferably carried out to the acrylic acid-containing solution because the heat-treatment of the present invention is preferably carried out in as many steps as possible. It should be noted that, the heat-treatment of the present invention to the acrylic acid-containing solution 35 may be carried out to the acrylic acid-containing solution 35 in the step B, or may be carried out to the acrylic acid-containing solution 35 in the step C to be described later. That is, the heat-treatment of the present invention may be carried out before introducing it to the high boiling point distillation column 70 in the step C, or may be carried out after introducing it to the high boiling point distillation column 70 in the step C.

By carrying out the heat-treatment of the present invention, use of expensive chemicals and the chemical treatment after use thereof like in the conventional method is not needed, and also, super purification by distillation or crystallization is not needed, therefore, increase of cost such as equipment cost or utilities cost can be suppressed, and impurities (particularly protoanemonin) in the process of acrylic acid can be reduced. Furthermore, contamination of acrylic acid caused by the impurities (particularly protoanemonin) can be alleviated, and the production method for acrylic acid having higher yield can be provided.

The heat-treatment of the present invention performing to the acrylic acid-containing solution 35 including protoanemonin obtained by collection is not particularly limited as long as temperature is 100° C. or more and time is 1 hour or more, however temperature is preferably 130° C. or more, more preferably 150° C. or more, further preferably 170° C. or more, and time is preferably 3 hours or more, more preferably 10 hours or more. Upper limit of treatment is not particularly limited; however, heating temperature is preferably 200° C. or less, more preferably 180° C. or less. In addition, heating time is preferably 50 hours or less, more preferably 20 hours or less.

By carrying out such heat-treatment of the present invention, even when about 100 to about 500 ppm by mass of protoanemonin is contained relative to the total mass of the acrylic acid-containing solution 35, said protoanemonin can be reduced preferably to 60% or less, more preferably 40% or less, further preferably 30% or less. It should be noted that, when the heat-treatment of the present invention is carried out for unnecessary long time, or is carried out at unnecessary higher temperature, acrylic acid as the desired compound may be dimerized, and the production efficiency of acrylic acid may be reduced, thus appropriate adjustment of temperature and time is needed.

It should be noted that, the mechanism of reducing protoanemonin significantly by heat-treatment of the present invention is not necessarily clarified, but is considered as following. That is, by the heat-treatment of the present invention, protoanemonin is considered to be changed to higher boiling point compound (anemonin, in case of dimerization,) by multimerization. Therefore, when the solution (this includes all substances generated in the production process of acrylic acid) containing protoanemonin and acrylic acid in the present invention is introduced to at least one step of each step described the present application, these substances behave as the higher boiling point substances. Such "high boiling point substances" exist at higher rate in the waste oil 78 discharged from the pyrolysis tank shown in FIG. 1, FIG. 2 to the outside of the system. In other word, existing ratio of protoanemonin in the product acrylic acid (60, 60') will be reduced. By giving an extreme example, if protoanemonin is assumed to be changed the absolutely non-volatile substance by the heat-treatment of the present invention, even when the target substances subjected to the heat-treatment of the present invention are returned to at least one step of each steps described herein, the protoanemonin can not be distilled in the product acrylic acid 60 (For example, in the FIG. 2 corresponding to the second embodiment of the first aspect of present invention, protoanemonin changed as non-volatile substance does not distill to the distillate side represented by 71). Therefore, the product acrylic acid 60 substantially containing no protoanemonin can be easily provided by the heat-treatment of the present invention. Therefore, "reduction" or "removal" in the present invention is not used as a concept of distilling away protoanemonin, but is used as a meaning of reducing or removing protoanemonin monomer by changing to the multimer of protoanemonin.

Specific method for the heat-treatment of the present invention can be carried out by referring to the conventional known knowledge or combining them, as long as the target substance subjected to the heat-treatment is heated at 100° C. or more, and the state thereof is maintained for 1 hour or more. Here, "1 hour or more" in the present invention, when the state in which the temperature of the target substance subjected to the heat-treatment is 100° C., maintains totally for 1 hour or more, it is included in the technical scope of the present invention. That is, even once heating is stopped and temperature is lowered 100° C., it is acceptable, provided that the state maintaining 100° C. is totally for 1 hour or more by heating again. Of course, continual heating for 1 hour or more is preferable considering from the production efficiency.

In addition, in the embodiment of the heat-treatment, for example, once the target substance subjected to the heat-treatment of the present invention is taken out to the outside of the system, and is introduced to the vessel (for example, heating vessel equipped with stirrer, columns and tanks equipped with heating means, piping equipped with heating means, vessels equipped with circulating pump instead of stirrer, equipped with heat exchanger as heating means), the target substance may be subjected to the heat-treatment of the present invention. It should be noted that, in the embodiment of taking out to the outside of the system, when the target substance is subjected to the heat-treatment of the present invention, this is preferably carried out in the vessel further equipped with the cooling device. By such a way, temperature and time in the heat-treatment can be completely controlled.

On the other hand, the target substance subjected to the heat-treatment of the present invention may be subjected to the heat-treatment of the present invention in the inside of the system without taking out to the outside of the system. There is an advantage that the heat-treatment of the present invention can be immediately carried out without the new additional equipment in this way.

It should be noted that, in the heat-treatment of the present invention, addition of polymerization inhibitor to the acrylic acid-containing solution 35 may be preferable. As the polymerization inhibitor, one kind or more compounds selected from the group consisting of N-oxyl compound, phenol compound, manganese salt such as manganese acetate, copper dialkyldithiocalbamate such as copper dibutyldithiocalbamate, nitroso compound, amine compound and phenothiazine may be included. The heat-treatment of the present invention can be more stably carried out by using N-oxyl compound or copper dialkyldithiocarbamate because both compounds can be effective in small amount.

Next, the acrylic acid-containing solution 35 subjected to the heat-treatment of the present invention (Of course, when the crude acrylic acid to be described later or residue of distillation is subjected to the heat-treatment of the present invention, the heat-treatment of the present invention to the acrylic acid-containing solution is not needed) is introduced to the inside of the system (here, the azeotropic distillation column 50) in order to supply the step C. However, before introducing it to the azeotropic distillation column 50, such acrylic acid-containing solution 35 is supplied to the acrolein diffusion column 31 to separate and treat acrolein, and the acrylic acid-containing solution 35' reduced the amount of acrolein from column bottom is preferably obtained. It is because that, in the acrylic acid-containing solution 35, acrolein as the raw material of acrylic acid may be contained. It should be noted that, when the distillate from the column top of acrolein diffusion column 31 is circulated to the column bottom of the collection column 30, acrylic acid distilled together with acrolein can be preferably effectively recycled.

The acrolein diffusion column 31 is not particularly limited, as long as acrolein can be separated, for example, packed column, shelf plate column (tray column) or the like can be used. Condition of diffusing acrolein can be appropriately selected from the various method for distillation, diffusion or the like depending on the containing acrylic acid concentration or acrolein concentration. In case of distillation, the column top pressure (absolute pressure) is 20 to 800 hPa, preferably 40 to 600 hPa, particularly preferably, 60 to 400 hPa. When the pressure is less than 20 hPa (absolute pressure), column, condenser, and vacuum equipment becomes larger size, then, equipment cost disadvantageously may increase. On the other hand, from the standpoint of polymerizability, pressure is preferably less than 800 hPa (absolute pressure). On the other hand, the column top temperature is generally 30 to 100° C., particularly preferably 40 to 80° C. On the other hand, the column bottom temperature is generally 40 to 110° C., particularly preferably 50 to 90° C. It should be noted that, in case of diffusion, acrolein can be separated by the conventionally known method.
(Step C)

Step C in the first embodiment of the first aspect of the present invention is a step obtaining the crude acrylic acid by introducing the acrylic acid-containing solution to the azeotropic distillation column and performing distillation.

The acrylic acid-containing solution 35', in which acrolein diffused, is introduced to the azeotropic distillation column to be distilled to obtain the crude acrylic acid. Of course, the acrylic acid-containing solution 35 may be directly introduced to the azeotropic distillation column 50 to obtain the crude acrylic acid without passing through the step of diffusing acrolein.

Condition of distillation in the azeotropic distillation column is not particularly limited and can be appropriately selected, provided that low boiling temperature substances such as water, acetic acid can be distilled.

The column top pressure (absolute pressure) of the azeotropic distillation column 50 is 10 to 400 hPa, preferably 15 to 300 hPa, particularly preferably 20 to 200 hPa. When the pressure is less than 10 hPs, column, condenser, vacuum equipment becomes larger size, then equipment cost disadvantageously increases. On the other hand, from the standpoint of polymerizability, pressure is preferably less than 400 hPa (absolute pressure).

In addition, the column top temperature of the azeotropic distillation column is generally 30 to 70° C., particularly 40 to 60° C. On the other hand, the column bottom temperature is generally 50 to 140° C., particularly 60 to 120° C.

As azeotropic solvent, the conventionally known solvent can be selected to use, in the present invention, toluene, heptane, methylcyclohexane, diethyl ketone, methyl propyl ketone, methyl isobutyl ketone, methyl t-butyl ketone, n-propyl acetate or the like can be used. These azeotropic solvents can be used alone or can be used as a mixture of combination with two or more kinds. These amounts can be appropriately selected to set up by person skilled in the art.

By distillation in the azeotropic distillation column 50, the low boiling point substance contained in the acrylic acid-containing solution 35' (for example, water, acetic acid, formaldehyde, formic acid or the like) can be discharged from the column top of the azeotropic distillation column 50. In the tank 50a, black part represents the aqueous layer, and white part represents the organic layer (this is the layer of circulating liquid composed of toluene mainly, and is circulating to the azeotropic distillation column). Here, by azeotropic dehydration, parts of water layer may be returned to 33' to use as the water 33' for collection. Component distilled from the column top of the azeotropic distillation column 50 does not include so much amount of acrylic acid (near to water). Therefore, this is used as the water 33' for collection. On the other hand, distillate 71 represented in the FIG. 2 to be described later includes acrylic acid significantly, thus, it is returned to the collection column 30 (preferably returned to lower part in the middle part of the column).

On the other hand, the crude acrylic acid can be obtained from the column bottom of the azeotropic distillation column 50. The crude acrylic acid obtained from the column bottom of the azeotropic distillation column 50 is the solution form (hereinafter, referred to "the solution of crude acrylic acid"), and in this solution of crude acrylic acid, although it is different depending on whether the acrylic acid-containing solution 35 is subjected to the heat-treatment of the present invention or not, when the heat-treatment is not carried out, about 100 to about 500 ppm of protoanemonin relative to the total mass of the crude acrylic acid solution may be contained.

Therefore, the crude acrylic acid containing protoanemonin in the column bottom of the azeotropic distillation column 50 is preferably subjected to the heat-treatment of the present invention. It should be noted that, as described above, when the acrylic acid-containing solution is subjected to the heat-treatment of the present invention, it is not essential that the crude acrylic acid is subjected to the heat-treatment of the invention. However, from the standpoint of producing the acrylic acid containing less amount of protoanemonin, the crude acrylic acid is preferably subjected to the heat-treatment of the present invention because the heat-treatment of the present invention is preferably carried out in as many steps as possible.

The heat-treatment of the present invention for the crude acrylic acid from the column bottom of the azeotropic distillation column 50 is not particularly limited, as long as temperature is 100° C. or more, time is 1 hour or more, preferably temperature is 130° C. or more, more preferably 150° C. or more, further preferably 170° C. or more, and time is preferably 3 hours or more, more preferably 10 hours or more. Upper limit is not limited, but the heating temperature is preferably 200° C. or less, more preferably 180° C. or less. Also, the heating time is preferably 50 hours or less, more preferably 20 hours or less.

By such heat-treatment of the present invention, when 100 to 500 ppm by mass of protoanemonin is contained, said protoanemonin can be preferably reduced to 60% or less, more preferably 40% or less, still more preferably 30% or less. Upper limit is not particularly limited; substantially it is about 70%.

When the heat-treatment of the present invention is carried out unnecessarily for longer time, or unnecessarily at higher temperature, acrylic acid as desired substance may be dimerized, and the production efficiency of acrylic acid may be reduced. Therefore, appropriate adjustment of temperature and time is needed.

(Step C')

Step C' in the first embodiment of the first aspect of the present invention includes a step of introducing the crude acrylic acid to the high boiling point distillation column to distill.

The crude acrylic acid obtained by step C is introduced to the inside of the system (here, the first high boiling point distillation column 70). This is because, in the crude acrylic acid obtained by step C, high boiling point substance such as acrylic acid dimer, maleic acid, protoanemonin, benzaldehyde, polymerization inhibitor except for high concentration of acrylic acid may be contained.

In step C' in the first embodiment of the first aspect of the present invention, the crude acrylic acid is supplied to the first high boiling point distillation column 70 for further purification, and the high boiling point substance (residue of distillation) is taken out from the column bottom and is recycled. On the other hand, high-purity acrylic acid 60' can be obtained from the column top. This acrylic acid 60' may be used as the product acrylic acid 60, or may be further purified aiming for higher purity. Specifically, it is shown below. That is, this acrylic acid 60' may contain trace amount of acrolein or furfural or the like. In this case, these substances are changed to the higher boiling point substances by using the aldehyde treatment agent such as hydrazine hydrate, and are distilled to increase of the purity of acrylic acid 60'.

The first high boiling point distillation column can use the packed column, the shelf plate column (the tray column) or the like.

Condition of distillation in the first high boiling point distillation column 70 is not particularly limited, as long as acrylic acid can be efficiently taken out from the column top, and high boiling point substance such as acrylic acid dimer, maleic acid, protoanemonin can be efficiently separated.

The column top pressure (absolute pressure) in the first high boiling point distillation column 70 is 10 to 400 hPa, preferably 15 to 300 hPa, particularly preferably 20 to 200 hPa. The reason comes from the fact that when the pressure is lower than 10 hPa (absolute pressure), column, condenser, vacuum equipment becomes large size, and much equipment cost is needed, thus this condition is disadvantageous. On the other hand, from the consideration of polymerizability, pressure less than 400 hPa (absolute pressure) is preferable.

In addition, the column top temperature of the first high boiling point distillation column 70 is generally 30 to 70° C., particularly 40 to 60° C. On the other hand, the column bottom temperature is generally 50 to 140° C., particularly 60 to 120° C.

(Step D)

Step D in first embodiment of the first aspect of the present invention includes a step of recovering the residue of distillation discharged from the first high boiling point distillation column.

In the column bottom liquid of the first high boiling point distillation column 70, acrylic acid dimer, maleic acid, and benzaldehyde are contained. But, in the column bottom liquid of this first high boiling point distillation column 70, several % by mass to about 50% by mass of acrylic acid is contained. Therefore, in order to improve the production yield of acrylic acid, acrylic acid is preferably recovered from the column bottom liquid to return to the inside of the system.

However, in the column bottom liquid of the first high boiling point distillation column 70, about 1,000 to about 5,000 ppm of protoanemonin relative to the total mass of the column bottom liquid may be contained, therefore, protoanemonin accompanied with recovered acrylic acid is returned to the inside of the system. Consequently, the heat-treatment of the present invention is preferably subjected to the column bottom liquid of the first high boiling point distillation column 70.

The heat-treatment of the present invention for the column bottom liquid of the first high boiling point distillation column 70 is different depending on whether the crude acrylic acid introduced from the azeotropic distillation column 50 is subjected to the heat-treatment of the present invention or not, in case of no heat-treatment, the heat-treatment is not particularly limited, as long as temperature is 100° C. or more, and time is 1 hour or more, but temperature is preferably 130° C. or more, more preferably 150° C. or more, further preferably 170° C. or more, and time is preferably 3 hours or more, more preferably 10 hours or more. Upper limit of the treatment is not particularly limited, but heating temperature is preferably 200° C. or less, more preferably 180° C. or less. In addition, heating time is preferably 50 hours or less, more preferably 20 hours or less.

By performing such heat-treatment of the present invention, protoanemonin contained in the column bottom liquid of the first high boiling point distillation column 70 can be preferably reduced to 60% or less, more preferably 40% or less, further preferably 30% or less.

When the heat-treatment of the present invention is carried out unnecessarily for longer time, or unnecessarily at higher temperature, acrylic acid as desired substance may be dimerized, thus, the production efficiency of acrylic acid may be reduced. Therefore, appropriate adjustment of temperature and time is needed.

It should be noted that, even after the column bottom liquid of the first high boiling point distillation column 70 is subjected to the heat-treatment of the present invention, acrylic acid dimer may be contained. Therefore, the column bottom liquid of the first high boiling point distillation column 70 subjected to the heat-treatment of the present invention is preferably pyrolyzed to acrylic acid by staying in pyrolysis tank 75 through the recovering column 80 of acrylic acid and thin-film evaporator 73 (these equipments are referred to "decomposition equipment of acrylic acid dimer"). It should be noted that, decomposition method for acrylic acid dimer is not particularly limited, as long as acrylic acid dimer can be decomposed to acrylic acid to recover as acrylic acid. For example, decomposition of acrylic acid dimer, and distillation of acrylic acid may be simultaneously carried out (refer to JP-B-61-35977, JP-B-61-36501 or the like), preferably the method by using the recovering column 80 of acrylic acid equipped with the thin-film evaporator parallel installed in combination pyrolysis tank 75 and plate column, is included (refer to JP-A-11-12222 or the like). It should be noted that, the column bottom liquid of the first high boiling point distillation column 70 subjected to the heat-treatment of the present invention may be directly introduced to the thin-film evaporator 73 without passing through the recovering column 80 of acrylic acid. However, bypassing through the recovering column of acrylic acid 80, acrylic acid can be recovered from this recovering column 80 of acrylic acid, and can be introduced to the first high boiling point distillation column 70 again, thus, this step is preferable from the standpoint of improving the yield of acrylic acid.

In said pyrolysis tank 75, acrylic acid dimer is decomposed at the temperature range of 120 to 220° C., and residence time (volume of the pyrolysis tank/amount of the waste oil) is different depending on the decomposition temperature, but it is set generally 0.1 to 60 hours. After decomposition of acrylic acid dimer to acrylic acid, this is circulated to the thin-film evaporator 73, and is returned to the first high boiling point distillation column 70 through the recovering column of acrylic acid 80, thus acrylic acid can be recovered from the column top of the first high boiling point distillation column 70. On the other hand, waste oil 78 is discharged from the pyrolysis tank 75.

It should be noted that, to said pyrolysis tank 75, decomposition catalyst such as alkaline metal salt, alkaline earth metal salt, and N-oxyl compound described in JP-A-2003-89672 can be added in the decomposition of acrylic acid dimer. When said N-oxyl compound is used as polymerization inhibitor in the collection step or the distillation step, this compound behaves as decomposition catalyst for acrylic acid dimer.

In FIG. 1, as the method for obtaining the acrylic acid-containing solution, the embodiment of using the collection column 30 was explained, however, in the present invention, the acrylic acid-containing solution may be obtained by using the condensation column. In order to obtain the acrylic acid-containing solution 35 by using the condensation column, the collection column 30 (includes the cooling tower 36, the cooling device 39 or the like) is replaced by the conventionally known condensation column, and then, the method can be carried out. Specific description for such method is omitted, but, for example, this method can be carried out by referring JP-W-2001-516737 or the like. It should be noted that, by using the condensation column, without using the solution 33' for collecting water or high boiling point solvent etc., mixed gas 6 is cooled rapidly by spray cooling device etc. equipped with the condensation column to obtain the acrylic acid-containing solution 35.

Second Embodiment

The second embodiment of the first aspect of the present invention is the production method for acrylic acid including:

A) a step of obtaining an acrylic acid-containing gas by catalytic gas-phase oxidation reaction of gas containing the acrylic acid raw material;

B) a step of obtaining an acrylic acid-containing solution by introducing the acrylic acid-containing gas to the collection column and performing collection;

C) a step of obtaining a crude acrylic acid by introducing the acrylic acid-containing solution to the crystallizer and performing crystallization, D) a step of recovering a mother liquid for crystallization discharged from the crystallizer;

C") a step of introducing the mother liquid for crystallization to the second high boiling point distillation column and performing distillation;

D') a step of recovering a residue of distillation discharged from the second high boiling point distillation column;

wherein a step of heat treating the acrylic acid-containing solution, the crude acrylic acid, the mother liquid for crystallization or the residue of distillation, containing 100 ppm by mass or more of protoanemonin, under the condition of 100° C. or more of temperature, 1 hour or more of time, and a step of introducing the acrylic acid-containing solution, the crude acrylic acid, the mother liquid for crystallization or the residue of distillation, having been heat treated, to the collection column, the second high boiling point distillation column or the crystallizer, are included in the production method.

The main different points between the first embodiment of the first aspect of the present invention and the second embodiment of the first aspect of the present invention are as follows.

The first different point is that the crude acrylic acid is obtained by crystallizer in the step C. The other point is that when the high boiling point impurities are distilled, the second high boiling point distillation column is used instead of the first high boiling point distillation column. It should be noted that, the condition of distillation setup in the second high boiling point distillation column is different from the condition of distillation setup in the first high boiling point distillation column, it is due to the difference of the component of the crude acrylic acid obtained by the low boiling point distillation column and the component of the crude acrylic acid obtained by crystallizer. However, both methods are just the same from the standpoint of removing high boiling point impurities.

Except the different point described above, explanation of first embodiment of the first aspect of the present invention applies for the second embodiment of the first aspect in a similar way, therefore, these explanation are omitted when it is not needed.

(Step A)

Step A of the second embodiment of the first aspect of the present invention is a step of obtaining an acrylic acid-containing solution by the catalytic gas-phase oxidation of the gas containing the acrylic acid raw material. In such step A, explanation of the first embodiment of the first aspect of the present invention applies in a similar way.

(Step B)

Step B of the second embodiment of the first aspect of the present invention is a step of obtaining an acrylic acid-containing solution by introducing the acrylic acid containing gas to the collection column and performing the collection. Such step B is conformed to the first embodiment of the first aspect of the present invention.

As for explanation of the aqueous solution 33 for collection and water 33 for collection, the above explanation applies in a similar way. However, in step B of the second embodiment of the first aspect of the present invention, further, distillate 71 discharged from the second high boiling point distillation column 70' or the mother liquid for crystallization may be circulated to the collection column 30 as the circulation liquid. The reason is that collection rate of acrylic acid can improve when acetic acid is introduced from the part other than the column top of the collection column 30. Concentration of acetic acid contained in the circulation liquid described above is 2% by mass or more, more preferably 2 to 20% by mass, particularly 3 to 15% by mass. When concentration of acetic acid is reduced less than 2%, variation effect of gas-phase distribution in the collection column 30 becomes low. Particularly, amount of circulated liquid is controlled so that amount of acetic acid to be introduced may be adjusted to 0.005 to 0.2 times of the mass flow of acrylic acid contained in the acrylic acid-containing gas, more preferably 0.008 to 0.15 times, particularly preferably 0.01 to 0.1 times. In some cases, acetic acid can be added newly. When amount of acetic acid becomes lower than 0.005 times, the improvement effect of collection efficiency of acrylic acid becomes useless. On the other hand, when amount of acetic acid becomes more than 0.2 times, it is difficult to obtain the high concentration of acrylic acid-containing solution because amount of acetic acid introducing to the collection column becomes very large.
(Step C)

Step C of the second embodiment of the first aspect of the present invention is a step of obtaining a crude acrylic acid by introducing the acrylic acid-containing solution to the crystallizer and performing the crystallization.

Firstly, crystallization will be explained.

Crystallization method to be used is not limited; each of continuous method and batch-wise method may be used. And crystallization can be carried out at one stage, or two or more stages. As continuous crystallizer, for example, column style BMC (Backmixing Column Crystallizer) crystallizer (manufactured by Nippon Steel Chemical Co., Ltd: Japan) integrated with a crystallization part, a solid-liquid separation part, and a crystal purification part; or crystallizer combined with as a crystallization part, for example, CDC (Cooling Disk Crystallizer) crystallizer (manufactured by GOUDA Co., Ltd: Holland) or the like, as a part of solid-liquid separation, for example, belt filter or centrifuge or the like, and as a part of crystal purification, for example, KCP (Kureha Crystal Purifier) purifying device (manufactured by Kureha-techno-engineering Co., Ltd) or the like can be used.

As a crystallizer 55, one combined with crystallizer, solid-liquid separation device, crystal purification device can be exemplified, and the method using continuous crystallizer is preferable. As a crystallization part, for example, equipment arranged as two sets of crystallizer (CDC) described in "Chemical Equipment (Kagaku Souchi), 2001, July, page 77 to 78", can be used. Each of crystallizer (1), (2) has a structure that the inside of the horizontal type crystallization tank is separated by several cooling plate in which open space of pathway is located underneath. Through this cooling plate, cooling and crystallization are carried out. Wiper for renewing the blade of stirring and the cooling transferring surface is equipped with stirring axis passing through the center of the cooling plate, and the liquid supplied from the throwing slot of the raw material liquid is transferred sequentially to the other end via the pathway located at the bottom of the cooling plate by stirring axis.

For example, when the acrylic acid-containing solution is supplied to the crystallization equipment (1), here, acrylic acid is crystallized, and belt-filter is used as a solid-liquid separation part, and after separating the crystal and the mother liquid, the mother liquid for crystallization is supplied to the crystallization equipment (2) to crystallize acrylic acid, and crystal and mother liquid can be separated by belt filter. Next, the crystal obtained by these crystallization equipment (1), (2) is introduced to the crystal purification part.

As crystal purification part, for example, crystal purification equipment (KCP) described in "Chemical Equipment (Kagaku Souchi), 2001, July, page 76 to 77", or JP-B-47-40621 can be used. For example, equipment in which screw conveyor is equipped at the center of the metallic tube, and melting device to melt crystal and slot for taking out the product after melting in the upper part, slot for taking out the liquid of residue in the lower part, and crystal supplying slot in column side part of lower part, are equipped respectively, can be exemplified. Crystal is conveyed to the column top of the purification column by screw conveyor, and is melted by melting device. The melting liquid is taken out from the slot of taking out product, and a part of liquid is dropped from the upper part of the purification column. By this dropping liquid, washing and sweating of crystal to be carried from the screw conveyor are carried out, and the liquid dropping from the upper part is taken out from the slot of taking out the residue of lower part. Amount of the above dropping liquid can be appropriately selected depending on purity of acrylic acid as desired substance.

The other advantageous embodiment of the present invention is the method for using batch-wise crystallizer. As such equipment, for example, layer crystallization equipment (dynamic crystallization equipment) manufactured by Sulzer Chemtech Co., Ltd, Switzerland or static crystallization equipment manufactured by BEFS PROKEM Co., Ltd, France can be used.

In the batch-wise method, needed plate number of crystallization depends on the needed purity. In the present invention, in order to obtain the high-purity acrylic acid, the purification step (dynamic crystallization step) is carried out 1 to 6 times, preferably 2 to 5 times, further preferably 2 to 4 times, and stripping step (dynamic crystallization step and/or static crystallization step) is carried out 0 to 5 times, preferably 0 to 3 times.

In addition, pre-purification may be carried out in advance before the step of crystallization purification. Pre-purification is carried out by crystallization. Therefore, pre-purification step and sequential purification step can be regarded as a series of crystallization step. In the pre-purification step, the pre-purification equipment combined with the crystallization equipment and the solid-liquid separation equipment can be used. As the crystallization equipment, CDC crystallization equipment, tank crystallization equipment or the like can be used, and as the solid-liquid separation equipment, belt filter, centrifuge or the like can be used.

One advantageous embodiment including the pre-purification of the present invention includes tank crystallization equipment and centrifuge, said tank crystallization equipment is composed of two tanks arranged in series, and are equipped with stirrer respectively, and the surfaces are composed of the double jacket, this jacket is controlled at constant temperature by thermostat. Firstly, the acrylic acid-containing solution is supplied to the first crystallization tank to crystallize the acrylic acid and the crystal is washed by using melting liquid after the separation of crystal and mother liquid by centrifuge.

In the step C of second embodiment of the first aspect of the present invention, the acrylic acid-containing solution is introduced to the crystallizer 55, and is crystallized one to two times to obtain the crude acrylic acid. In order to obtain the product acrylic acid having further reduced protoanemonin, the crude acrylic acid obtained via this crystallizer 55 can be subjected to the heat-treatment. By repeating further crystallization in the crystallizer 55, the product acrylic acid having higher purity can be obtained. Preferable number of crystallization to obtain the product acrylic acid is shown as described above.

(Step D)

In step D of the second embodiment of the first aspect of the present invention, the mother liquid of crystallization discharged from the crystallizer is recovered.

Even in this mother liquid of crystallization, although it is different depending on whether the acrylic acid-containing solution or the crude acrylic acid is subjected to the heat-treatment of the present invention or not, when the heat-treatment is not carried out, about 1,000 to about 10,000 ppm by mass of protoanemonin may be contained relative to the total mass of the mother liquid of crystallization.

Therefore, the mother liquid of crystallization containing protoanemonin is preferably subjected to the heat-treatment of the present invention.

The heat-treatment of the present invention for the mother liquid of crystallization is not particularly limited, as long as temperature is 100° C. or higher, and time is 1 hour or more, however the temperature is preferably 130° C. or higher, more preferably 150° C. or higher, further preferably 170° C. or higher, and time is preferably 3 hours or more, more preferably 10 hours or more. Upper limit of the condition is not particularly limited, however, heating temperature is preferably 200° C. or lower, more preferably 180° C. or lower. In addition, heating time is preferably 50 hours or less, more preferably 20 hours or less.

By such heat-treatment of the present invention, even when about 1,000 to about 10,000 ppm by mass of protoanemonin is contained relative to the total mass of the mother liquid of crystallization, said protoanemonin can be preferably reduced to 60% or less, more preferably reduced to 40% or less, further preferably reduced to 30% or less. Upper limit is not particularly limited, but substantially about 70%.

When the heat-treatment of the present invention is carried out for unnecessarily longer time, or at unnecessarily higher temperature, acrylic acid as the desired substance may be dimerized, and the production efficiency of acrylic acid may be reduced, thus appropriate adjustment of temperature and time is needed.

(Step C'')

In step C'' of the second embodiment of the first aspect of the present invention, the mother liquid of crystallization is introduced to the second high boiling point distillation column to distill.

In the second high boiling point distillation column 70', the packed column or the shelf plate column (the tray column) or the like can be used.

Condition of distillation in the second high boiling point distillation column 70' is not particularly limited, as long as acrylic acid can be efficiently taken out from the column top, and the high boiling point substances such as acrylic acid dimer, maleic acid, protoanemonin can be efficiently removed.

In addition, the pressure of the column top in the second high boiling point distillation column 70' (absolute pressure) is 10 to 400 hPa, preferably 15 to 300 hPa, particularly preferably 20 to 200 hPa. When the pressure is less than 10 hPa (absolute pressure), column, condenser, and vacuum equipment becomes large size, and much equipment cost is needed, thus this condition is disadvantageous. On the other hand, from the standpoint of polymerizability, pressure less than 400 hPa (absolute pressure) is preferable. In addition, the temperature of the column top of the second high boiling point distillation column 70' is generally 30 to 70° C., particularly 40 to 60° C. On the other hand, the temperature of the column bottom is generally 50 to 140° C., particularly 60 to 120° C.

It should be note that, as described above, distillate 71 discharged from the second high boiling point distillation column 70', and the mother liquid of crystallization may be circulated to the collection column as the circulated liquid.

(Step D')

In step D' of the second embodiment of the first aspect of the present invention, the residue of distillation discharged from the second high boiling point distillation column is recovered.

By distilling under the condition of step C'', the gas containing vaporized acrylic acid is distilled from the column top of the second high boiling point distillation column 70' to become the distillate 71. In addition, this is preferably introduced (circulated) to the collection column.

On the other hand, in the column bottom liquid of the second high boiling point distillation column 70', acrylic acid dimer, maleic acid, benzaldehyde or the like are contained. However, acrylic acid is contained in the column bottom liquid of the second high boiling point distillation column 70'. Consequently, in order to improve the production efficiency of acrylic acid, acrylic acid is preferably recovered from the column bottom liquid, and is returned to the inside of the system. However, in the liquid of column bottom of the second high boiling point distillation column 70', about 1,000 to about 10,000 ppm of protoanemonin may be contained relative to the total mass of such column bottom liquid. Therefore, the column bottom liquid of the second high boiling point distillation column 70' is preferably subjected to the heat-treatment of the present invention.

In the heat-treatment of the present invention for the liquid of column bottom of the second high boiling point distillation column 70', although it is different depending on whether the heat-treatment of the present invention carried out on the other time point or not, when the heat-treatment is not carried out, condition of the heat-treatment is not particularly limited, as long as temperature is 100° C. or higher, and time is 1 hour or more, but temperature is preferably 130° C. or more, more preferably 150° C. or more, further preferably 170° C. or more, time is preferably 3 hours or more, more preferably 10 hours or more. Upper limit of the condition is not particularly limited, but heating temperature is preferably 200° C. or less, more preferably 180° C. or less. In addition, heating time is preferably 50 hours or less, more preferably 20 hours or less.

By such heat-treatment of the present invention, even when 1,000 to 10,000 ppm by mass of protoanemonin is contained relative to the total mass of the column bottom liquid of the second high boiling point distillation column 70', said protoanemonin can be preferably reduced to 60% or less, more preferably reduced to 40% or less, further preferably reduced to 30% or less.

When the heat-treatment of the present invention is carried out for unnecessarily longer time, or at unnecessarily higher temperature, acrylic acid as the desired substance may be dimerized, and the production efficiency of acrylic acid may be reduced, thus appropriate adjustment of temperature and time is needed.

Figure 2:
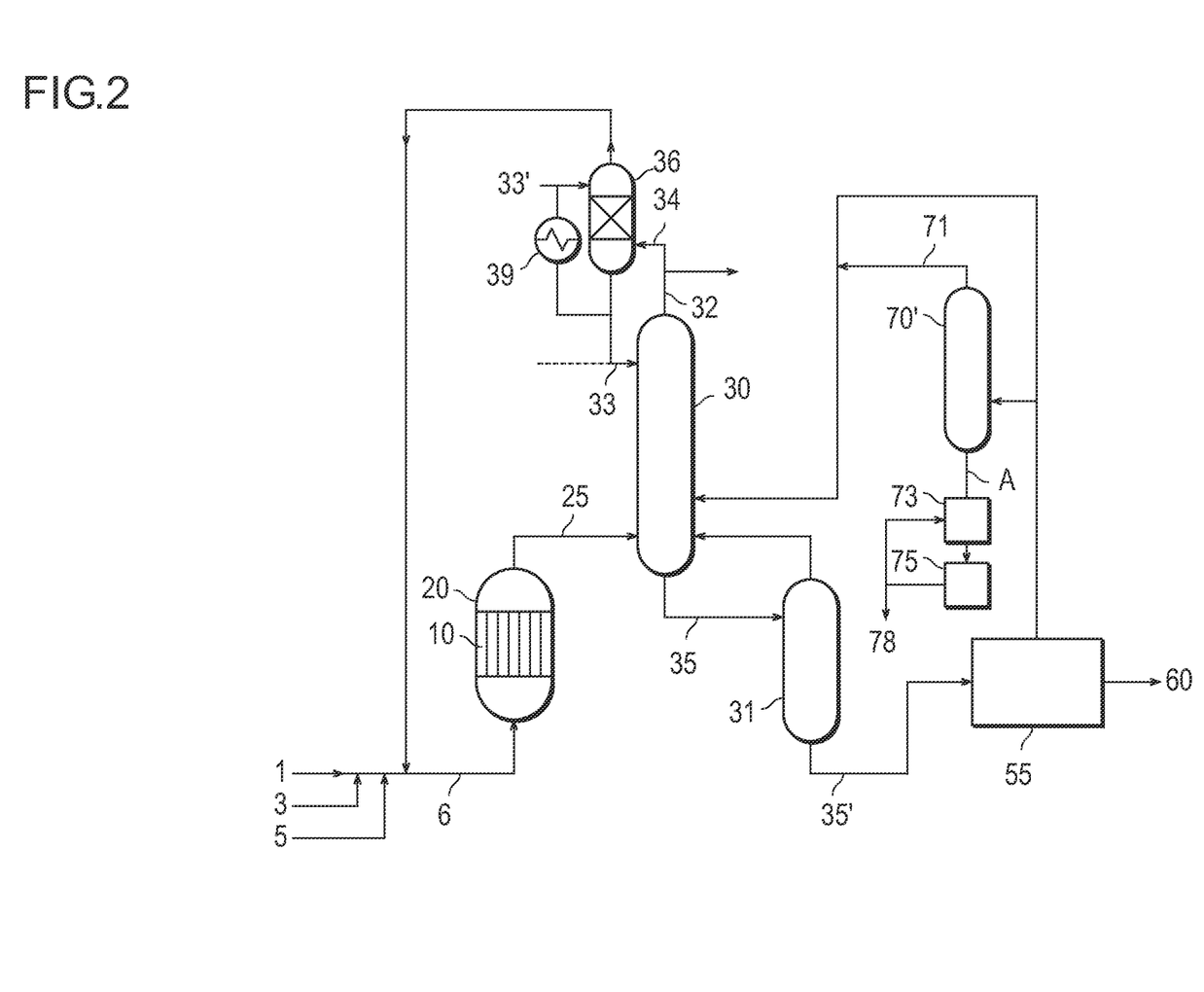
FIG. 2 is the schematic diagram showing the production equipment to be used in the second embodiment of the first production method for acrylic acid of the present invention.

It should be noted that, the acrylic acid recovering column 80 equipped described in the first embodiment of the first aspect of the present invention may be intervened at the point shown at A in FIG. 2 to treat the column bottom liquid of the second high boiling point distillation column 70'. By adapting this method, yield of acrylic acid is improved. Subsequently, as described above, step of the thin-film evaporator 73 and step of the pyrolysis tank 75 may be performed. The reason is shown as described above.

Thus, in the present invention, the specific heat-treatment of the present invention is very advantageously carried out in the various points of the system of producing acrylic acid. This point may be one of the characteristics of the present invention.

In the above, the condition of the heat-treatment of the present invention at each point of steps of the production method for acrylic acid of the present invention, and the reduction of amount of protoanemonin were described.

The explanation will be given below from the standpoint of the efficient reduction of protoanemonin.

From the standpoint of reducing protoanemonin efficiently, amount of protoanemonin contained in the target substance to be subjected to the heat-treatment is preferably 100 ppm by mass, more, preferably 200 ppm by mass, further preferably 500 ppm by mass, particularly preferably 1,000 ppm by mass relative to the total mass of the target substance. Upper limit is not particularly limited, but is 50,000 ppm or less.

When amount of protoanemonin contained in the target substance to be subjected to the heat-treatment is less than 100 ppm, it is not efficient because amount to be reduced of protoanemonin is small even if the heat-treatment of the present invention is carried out. That is, contamination of acrylic acid by protoanemonin can not be efficiently alleviated. Therefore, amount of protoanemonin contained in the target substance to be subjected to the heat-treatment is preferably 100 ppm by mass or more. It should be noted that, when both of "the acrylic acid-containing solution" and "crude acrylic acid" are subjected to the heat-treatment of the present invention, concentration of protoanemonin relative to the total mass of these total mixed solutions is preferably 100 ppm or more. On the other hand, when amount of protoanemonin to be subjected to the heat-treatment is 1,000 ppm or more, protoanemonin can be efficiently reduced when the heat-treatment of the present invention is carried out. That is, contamination of acrylic acid by protoanemonin can be efficiently alleviated.

From the standpoint of efficient reduction of protoanemonin, after the heat-treatment of the present invention, this is preferably reduced 50% by mass, more preferably 60 to 90% by mass.

That is, by performing the heat-treatment of the present invention to the solution containing protoanemonin and acrylic acid in the present invention (including all the solution produced in acrylic acid producing process of the present invention), content of protoanemonin can be preferably reduced 60% or less, more preferably 40% or less, further preferably 30% or less relative to the solution containing protoanemonin and acrylic acid before the heat-treatment. However, it may substantially include 5% or more of protoanemonin.

Considering from the above standpoint, temperature of the heat-treatment of the present invention is preferably 100° C. or more, more preferably 130° C. or more, further preferably 150° C. or more, particularly preferably 170° C. or more. It should be note that, upper limit is preferably 200° C. or less.

In addition, time of the heat-treatment of the present invention is preferably 1 hour or more, more preferably 3 hours or more, further preferably 10 hours or more. It should be noted that, upper limit is preferably 50 hours or less.

From the above standpoint, in the present invention, the method for efficiently alleviating the contamination of acrylic acid by protoanemonin can be provided. That is, in the present invention, the method for efficiently reducing or removing protoanemonin in the production method for acrylic acid can be provided.

It should be noted that, amount of protoanemonin contained in acrylic acid 60 as the final product is preferably 10 ppm by mass or less, more preferably 5 ppm by mass or less, further preferably 2 ppm by mass or less. However, amount of protoanemonin may be substantially 0.1 ppm or more.

The Second Aspect of the Present Invention

The second aspect of the present invention is the production method for hydrophilic resin including the polymerization of monomer component containing acrylic acid obtained by the first aspect of the present invention.

The Third Aspect of The Present Invention

The third aspect of the present invention is the production method for water-absorbing resin including the polymerization of monomer component containing acrylic acid obtained by the first aspect of the present invention.

When acrylic acid obtained by the first aspect of the present invention is used as a raw material for the production of water-absorbing resin or water-soluble resin, polymerization reaction is easy to be controlled, and quality of the resultant hydrophilic resin is stable, water-absorbability, various properties of dispersion agent of inorganic materials can be improved. Particularly, when acrylic acid obtained by the first aspect of the present invention is used as the raw material for the production of water-absorbing resin, polymerization reaction can be easily controlled, water-absorbability of the resultant water-absorbing resin can be improved.

The preferable embodiment is described as follows.

By using acrylic acid and/or salt thereof obtained by the present invention as the main component (preferably 70 mol % or more, more preferably 90 mol % or more) of monomer, further, about 0.001 to about 5 mol % (value relative to acrylic acid) of cross-linking agent, and about 0.001 to about 2 mol % of initiator of radical polymerization, cross-linking polymerization is carried out, then drying and pulverizing are performed to obtain the water-absorbing resin.

Water-absorbing resin means the water-swelling and water-insoluble polyacrylic acid resin having the structure of cross-linking, which can absorb 3 (three) times or more, preferably 10 to 1,000 times of pure water or normal saline solution of own weight, and forms the water-insoluble hydrogel having water soluble component (water soluble part) of preferably 25% by mass or less, more preferably 10% by mass or less. Exemplification and measuring method for physical properties of such water-absorbing resin are exemplified, for example, by U.S. Pat. No. 6,107,358, U.S. Pat. No. 6,174,978, and U.S. Pat. No. 6,241,928 respectively.

In addition, as the method of improving productivity, for example, U.S. Pat. No. 6,867,269, U.S. Pat. No. 6,906,159, U.S. Pat. No. 7,091,253, WO-01/038402, and WO-2006/034806 can be exemplified.

The series of step of producing water-absorbing resin by using acrylic acid as the raw material, and neutralizing, polymerizing, drying or the like is described as follows.

Part of acrylic acid obtained by the production method of the present invention is supplied to the production process of water-absorbing resin via line. In the production process of water-absorbing resin, said acrylic acid is subjected to the desired treatment by introducing to neutralization step, polymerization step, drying step, consequently, water-absorbing resin can be produced. Desired treatment may be carried out to improve the various physical properties, for example, cross-linking step may be intervened during polymerization or after polymerization.

Neutralization step is an optional step, for example, mixing method of the powder or aqueous solution of determined amount of basic substance and acrylic acid, or resultant acrylic acid (salt) is exemplified. However, this method is not particularly limited, therefore, the known method can be employed. It should be noted that, neutralization step may be carried out before polymerization or after polymerization, in addition, may be carried out both before and after polymerization. As basic substance to be used in the neutralization of acrylic acid, for example, the known basic substance such as (hydrogen) carbonate, hydroxide of alkaline metal, ammonia, and organic amine may be used. In addition, neutralization ratio of polyacrylic acid is not particularly limited, but may be adjusted to obtain the optional neutralization ratio (for example, 30 to 100 mol % of optional value).

Polymerization method in the polymerization step is not particularly limited, and the known method such as polymerization by radical polymerization initiator, radiation polymerization, polymerization by irradiation of electron-beam or active energy ray, ultraviolet-ray polymerization by photo-sensitizer may be used. In addition, various condition such as polymerization initiator or polymerization condition can be optionally selected. Of course, when needed, the known additive agent such as cross-linking agent or the other monomer, further, water-soluble chain transfer agent or hydrophilic polymer may be added.

Acrylic acid salt type polymer (hereinafter, referred to "water-absorbing resin") after polymerization is subjected to the drying step. The drying method is not particularly limited, and the known drying means such as hot air dryer, fluidized-bed dryer, and Nauta dryer can be used, and water-absorbing resin can be appropriately dried at the desired drying temperature (preferably 70 to 230° C.)

Water-absorbing resin obtained through the drying step may be used as it is, or, further, may be granulated, pulverized, or surface cross-linked, in addition, can be provided to the appropriate application by further adding various additives such as reducing agent, perfume material, or binder.

EXAMPLE

Example 1

Propylene as acrylic acid raw material, air as the molecular oxygen-containing gas, dilution-gas, and mixed gas obtained by catalytic gas-phase oxidation were introduced to the collection column, and were contacted with water as aqueous solution for collection to obtain the acrylic acid-containing solution.

Subsequently, the acrylic acid-containing solution was introduced to the diffusion column of acrolein to diffuse acrolein, and the acrylic acid-containing solution in which acrolein was diffused, was obtained Subsequently, this acrylic acid-containing solution was supplied to the low-boiling point distillation column (the azeotropic distillation column), and the low-boiling point impurities such as water, acetic acid were removed by distillation using toluene as azeotropic solvent to obtain the crude acrylic acid containing 250 ppm by mass of protoanemonin.

It should be noted that, content of protoanemonin was determined by using liquid chromatography (manufactured by Shimadzu Corp.; model number: SCL-10Avp). In the other examples, comparative examples, the same method was employed.

500 g of this crude acrylic acid was charged to the flask equipped with stirrer. The heat-treatment was carried out by maintaining the temperature of the flask at 100° C., stirring in 20 hours. As a result, content of protoanemonin in the crude acrylic acid after the heat-treatment became 90 ppm by mass.

Therefore, by introducing the crude acrylic acid after this heat-treatment to the inside of the system (particularly, any one of the collection column, the azeotropic distillation column), contamination by protoanemonin in the process for producing acrylic acid can be alleviated.

Example 2

By introducing the crude acrylic acid (no-heat treatment of the present invention) described in Example 1 to the first high-boiling point distillation column to remove the high-boiling point impurities such as maleic acid or acrulic acid dimer, purified acrylic acid was obtained from the column top.

On the other hand, the residue of distillation containing 1,500 ppm by mass of protoanemonin was obtained from the column bottom of such high-boiling point distillation column.

500 g of this crude acrylic acid (the residue of distillation) was charged to the flask equipped with stirrer. The heat-treatment was carried out by maintaining the temperature of the flask at 150° C., stirring for 5 hours. As a result, content of protoanemonin in the residue of distillation after the heat-treatment became 260 ppm by mass.

Therefore, by introducing the residue of distillation after the heat-treatment to the inside of the system (particularly, any one of the collection column, the azeotropic distillation column), contamination by protoanemonin in the process for producing acrylic acid can be alleviated.

Example 3

Propylene as acrylic acid raw material, air as the molecular oxygen-containing gas, dilution-gas, and mixed gas obtained by catalytic gas-phase oxidation were introduced to the collection column, and were contacted with water to obtain the acrylic acid-containing solution.

Subsequently, the acrylic acid-containing solution was introduced to the crystallizer to obtain the crude acrylic acid, also, the mother liquid of crystallization was taken out from the crystallizer.

Subsequently, the mother liquid of crystallization was supplied to the second high-boiling point distillation column, and the high-boiling point impurities such as maleic acid, acrylic acid dimer were removed to recover the purified acrylic acid from the column top, as well as to obtain the crude acrylic acid containing 1,700 ppm by mass of protoanemonin from the column bottom.

500 g of this crude acrylic acid was charged to the flask equipped with stirrer. The heat-treatment was carried out by maintaining the temperature of the flask at 170° C., stirring for 5 hours. As a result, content of protoanemonin in the crude acrylic acid after the heat-treatment was 290 ppm by mass.

Therefore, by introducing the acrylic acid-containing solution after the heat-treatment to the inside of the system (particularly, any one of the collection column, crystallizer, the second high-boiling point distillation column), contamination by protoanemonin in the process for producing acrylic acid can be alleviated.

Comparative Example 1

Except that heating time of the heat-treatment is set to 0.5 hours, the heat-treatment of the crude acrylic acid was carried out by the procedure similar to example 1.

As a result, content of protoanemonin in acrylic acid after the heat-treatment was 240 ppm by mass.

Comparative Example 2

Except that heating temperature of the heat-treatment is set to 50° C. hours, the heat-treatment of acrylic acid was carried out by the procedure similar to example 1. As a result, content of protoanemonin in acrylic acid after the heat-treatment was 250 ppm by mass without change.

It should be noted that, the present application is based on JP-A-2008-116504 filed on Apr. 27, 2008. The disclosed content is hereby incorporated by reference in its entirety.

DESCRIPTION OF REFERENCE NUMERICAL

1: acrylic acid raw material;
3: molecular oxygen-containing gas;
5: dilution gas;
6: the mixed gas;
10: catalytic gas-phase oxidation catalyst;
20: reactor;
25: acrylic acid-containing gas;
30: collection column;
31: acrolein diffusion column;
32: exhaust gas from column top of the collection column;
33: aqueous solution for collection;
33': water for collection;
34: recycled gas;
35, 35': acrylic acid-containing solution;
36: cooling tower;
39: cooling device;
50: low-boiling point distillation column (the azeotropic distillation column);
50a: tank;
53: pre-purification separation device;
55: crystallizer;
60: product acrylic acid;
60': high-purity acrylic acid;
70: first high-boiling point distillation column:
70': second high-boiling point distillation column:
71: distillate;
73: thin-film evaporator;
75: pyrolysis tank;
78: waste oil;
80: acrylic acid recovering column;

The invention claimed is:

1. Production method for acrylic acid comprising:
A) a step of obtaining an acrylic acid-containing gas by catalytic gas-phase oxidation reaction of a gas containing an acrylic acid raw material;
B) a step of obtaining an acrylic acid-containing solution by introducing the acrylic acid-containing gas to a collection column or a condensation column and performing collection or condensation; and
C) a step of obtaining a crude acrylic acid by introducing the acrylic acid-containing solution to a distillation column or a crystallizer and performing distillation or crystallization,
C') a step of obtaining acrylic acid product by introducing the crude acrylic acid from the distillation column into a high boiling point distillation column for further distilling, or by introducing the crude acrylic acid from the crystallizer to a crystallizer for further crystallizing;
wherein a step of heat treating the acrylic acid-containing solution or the crude acrylic acid, containing 100 ppm by mass or more of protoanemonin, under the condition of 100° C. or more of temperature, 1 hour or more of time; and a step of introducing the acrylic acid-containing solution or the crude acrylic acid, having been heat treated, to the collection column, the condensation column, the distillation column or the crystallizer, are included in the production method wherein the step of heat treating decreases the amount of protoanemonin to 60% or less of that before the heat treatment.

2. The production method for acrylic acid according to claim 1, further comprising:
D) a step of recovering a residue of distillation or a mother liquid of crystallization discharged from the distillation column or the crystallizer;
wherein a step of heat treating the acrylic acid-containing solution, the crude acrylic acid, the residue of distillation or the mother liquid of the crystallization, containing 100 ppm by mass or more of protoanemonin, under the condition of 100° C. or more of temperature, 1 hour or more of time; and a step of introducing the acrylic acid-containing solution, the crude acrylic acid, the residue of distillation or the mother liquid of the crystallization, having been heat treated, to the collection column, the condensation column, the distillation column or the crystallizer, are included in the production method.

3. A production method for a hydrophilic resin wherein a monomer component containing acrylic acid obtained by the production method set forth in claim 1 is polymerized.

4. A production method for water-absorbing resin wherein a monomer component containing acrylic acid obtained from the production method set forth in claim 1 is polymerized.

* * * * *